United States Patent
Glaser et al.

(10) Patent No.: US 6,331,431 B1
(45) Date of Patent: *Dec. 18, 2001

(54) VACUUM DEVICE AND METHOD FOR ISOLATING PERIPLASMIC FRACTION FROM CELLS

(75) Inventors: Scott M. Glaser, San Diego; William D. Huse, Del Mar; William P. MacConnell, Cardiff, all of CA (US)

(73) Assignee: Ixsys, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/563,654

(22) Filed: Nov. 28, 1995

(51) Int. Cl.[7] ............... B01D 35/00; C12N 1/06; C12N 1/02; C12M 1/00
(52) U.S. Cl. ............... 435/261; 210/406; 422/101; 422/102; 435/259; 435/283.1; 435/308.1
(58) Field of Search ............... 435/259, 261; 210/406; 422/101, 102

(56) References Cited

U.S. PATENT DOCUMENTS

| | | | |
|---|---|---|---|
| 4,306,514 | * 12/1981 | Bouclier | 118/52 |
| 4,327,661 | * 5/1982 | Boeckel | 118/52 |
| 5,205,989 | * 4/1993 | Aysta | 422/101 |

OTHER PUBLICATIONS

Zweibel et al, "Polycrystalline thin–film . . . ", 1984, see abstract.*

FiltaPlates: Polyfiltronics, 150 Weymouth Street; Rockland, MA 02370.

Silent Monitor Loprodyne 1.2 m membrane–bottomed plates: Pall Corporation; Portsmouth, England.

Easy–Titer Elifa System: Pierce; 3747 N. Meridian Rd.; P.O. Box 117; Rockford, IL 61105.

Environmental Shaker: Baxter Diagnostics, Inc.; Scientific Products Division; 1430 Waukegan Road; McGaw Park, IL 60085-6787.

Bio–Block–96 Deep Well: DBM Scientific, 511 Fifth Street; San Fernando, CA 91340.

Chang et al., "Expression of Antibody Fab Domains on Bacteriophage Surfaces: Potential Use for Antibody Selection," *J. Immunol.* 147(10):3610–3614 (1991).

Gram et al., "In Vitro Selection and Affinity Maturation of Antibodies from a Naive Combinatorial Immunoglobulin Library," *Proc. Natl. Acad. Sci. USA* 89:3576–3580 (1992).

Hawkins et al., "Selection of Phage Antibodies by Binding Affinity: Mimicking Affinity Maturation," *J. Mol. Biol.* 226:889–896 (1992).

Huse et al., "Application of a Filamentous Phage pVIII Fusion Protein System Suitable for Efficient Production, Screening, and Mutagenesis of F(ab) Antibody Fragments," *J. Immunol.* 149(12):3914–3920 (1992).

* cited by examiner

*Primary Examiner*—David M. Naff
*Assistant Examiner*—Deborah K. Ware
(74) *Attorney, Agent, or Firm*—Campbell & Flores LLP

(57) ABSTRACT

A high throughput device is provided for simultaneously isolating periplasmic fractions from multiple samples of host cells. The device can be formatted to operate in a series. A method for simultaneously isolating multiple periplasmic fractions is also provided. The method includes (a) providing a high throughput device for isolating periplasmic fractions from multiple samples of host cells having an outer membrane via attaching a removable sample chamber having a membrane chamber wall to a vacuum chamber and applying a vacuum thereto (b) removing media with the vacuum and (c) removing the outer membrane of the host cells (d) attaching a collection chamber to the vacuum chamber and applying a vacuum thereto in order to carry out a collection of the periplasmic fractions that pass through the membrane of the chamber wall from the host cells. A workstation is also provided which includes one or more high throughput devices for simultaneously isolating periplasmic space fractions from a plurality of samples of host cells, and a device for simultaneously culturing a plurality of samples. preferably the membrane of the chamber is a neutral nylon membrane having an average pore diameter of 1 to 1.2 micron.

23 Claims, 7 Drawing Sheets

VACUUM DEVICE AND METHOD FOR ISOLATING PERIPLASMIC FRACTION FROM CELLS

Throughout this application various publications are referenced within parentheses. The disclosures of these publications in their entireties are hereby incorporated by reference in this application in order to more fully describe the state of the art to which this invention pertains.

BACKGROUND OF THE INVENTION

The present invention relates generally to the expression and isolation of proteins expressed in the periplasmic space of bacteria and, more particularly, to methods of simultaneously isolating periplasmic fractions from multiple samples of host cells.

With the advent of recombinant DNA technology the demand for rapid and efficient methods of recombinant protein expression has increased steadily over the years. This demand has resulted in a detailed understanding of essential elements and requirements for expression in both procaryotic and eukaryotic systems. It is now routine for one skilled in the art to express essentially any desired protein coding sequence as a recombinant protein in various different hosts including bacteria, yeast, insect cells and mammalian cells.

The available systems for recombinant expression have similarly evolved to keep pace with the increasing demand. For example, there are numerous vectors available for efficient expression of protein coding sequences, such as cDNA, as soluble fusion proteins or authentic sequences without a fusion partner in *E. coli* or other bacteria. Specific examples of such expression vectors include the T7, tac or Lac UV5 vectors. Many vectors also include characteristics which enable the enrichment or purification of the recombinant protein. Most of these modifications fuse an affinity tag to the recombinant sequence for subsequent purification by affinity chromatography of the cell extract or of the secreted protein into the growth medium. Some vectors also include protease cleavage sites to remove the fusion partner from the recombinant sequence. Many other attributes have also been incorporated into various expression vectors and systems to meet the desired needs of a particular application. Moreover, one skilled in the art can routinely engineer and construct various modifications to these systems, or construct novel systems tailored to the needs and desired outcome for a particular application.

Expression vectors and systems have also been devised which direct expression of recombinant proteins to specific locations. Directed expression to particular locations offers specific advantages over expression of soluble fusion proteins described above. For example, systems have been devised which allow for the surface expression of recombinant proteins on the inner membrane of *E. coli*, to the periplasmic space of bacteria, or on the coat of bacteriophage. Expression in the periplasmic space allows for a enriched source of starting material which is partially free of contaminating cellular material. The advantage of surface expression is that it allows for the direct and simultaneous isolation of an unknown protein and its encoding nucleotide sequence (Chang et al., *J. Immunol.* 147:3610–3614 (1991); Gram et al., *Proc. Natl. Acad. Sci. USA* 89:3576 (1992); Hawkins et al., *J. Mol. Biol.* 226:889 (1992); and Huse et al., *J. Immunology* 149:3914 (1992)).

Systems similar to those described above for recombinant expression in procaryotic systems have also been developed for systems which include species as diverse as insect cells to mammalian cells. Moreover, recombinant protein expression has also been, and is expected to continue to be a major component in the commercial development of new biological-based drugs. The most successful recombinant proteins being used as therapeutics include erythropoietin, G-CSF, interferons, growth factors, interleukin 1 and monoclonal antibodies. In addition to the use of recombinant proteins as therapeutics, essentially all biotechnology companies and most pharmaceutical companies rely heavily on the use of recombinant expression within their research and development and product development programs. Such uses range from protein expression for antibody production and functional studies to the creation of mutagenized species for identifying enhanced functional characteristics to the generation of large libraries of peptides and antibodies for drug screening and genes for reconstructing biosynthetic pathways.

Regardless of the advances of recombinant expression, there remains one major disadvantage associated with all of these systems and especially those utilized for drug discovery of biopharmaceuticals. This disadvantage is the need to identify and characterize the active components present in the cell extract. For example, identification of lead proteins requires the preparation of sufficient quantities of active protein samples for analysis by a variety of techniques such as binding assays, enzyme kinetics, inhibition assays, growth assays and signal transduction. It is the screening of large libraries that can be labor intensive. Purification methods usually rely on standard biochemical or immunoaffinity techniques which are labor intensive and require multiple time consuming steps. Such drawbacks rapidly become burdensome when recombinant expression and purification is coupled to a high throughput process such as those necessary in the biotechnology and drug development industries.

Thus, there exists a need for the efficient and simultaneous isolation of recombinant proteins from multiple samples of host cells. The present invention satisfies this need and provides related advantages as well.

SUMMARY OF THE INVENTION

The invention provides a high throughput device for simultaneously isolating periplasmic fractions from multiple samples of host cells. The high throughput device consists of a vacuum chamber having one end open, a means for supporting a collection chamber and a vacuum aperture. The open end of the vacuum chamber contains a means for supporting a sample chamber which can be sealed under vacuum. The device can be formatted to operate more than one in series. The invention also provides a device for simultaneously culturing of a plurality of samples. This culture device consists of a bottom component having a means for supporting a plurality of multi-well culture chambers, a top component attached to the bottom component by substantially vertical supports and a means for attaching the culture device to a platform of a shaker or orbital incubator. Also provided is a method for simultaneously isolating periplasmic fractions from multiple samples of host cells. The method consists of: (a) providing a high throughput device for simultaneously isolating periplasmic fractions from multiple samples of host cells having a vacuum chamber containing one end open, a means for supporting a collection chamber and a vacuum aperture, the open end of the vacuum chamber having a means for supporting a sample chamber which can be sealed under vacuum; (b) attaching the sample chamber containing a sample of host cells in media to the vacuum chamber; (c) applying a vacuum to the vacuum chamber to remove the media; (d) removing the outer membrane of the host cells; (e) attaching a collection chamber to the vacuum chamber; and (f) applying a vacuum to the vacuum chamber to collect the periplasmic fraction from the host cells. A workstation is also provided. The workstation consists of one or more high throughput devices for simultaneously isolating periplasmic space fractions from a plurality of samples of host cells and a device for simultaneously culturing a plurality of samples.

DETAILED DESCRIPTION OF THE INVENTION

Figure 1:
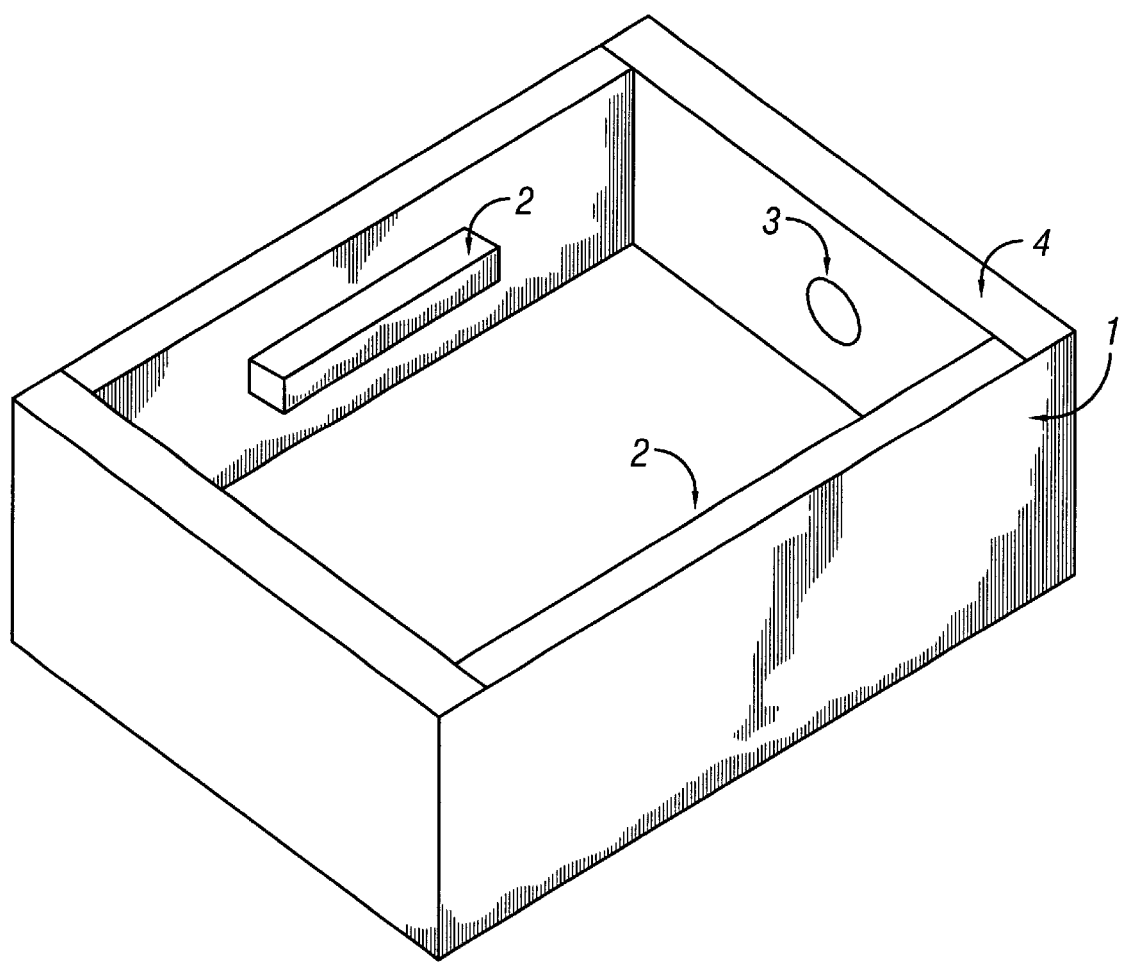
FIG. 1 is a schematic of a high throughput device for simultaneously isolating periplasmic fractions which exemplifies the open end of the vacuum chamber for supporting a collection chamber and a sample chamber.

This invention is directed to a simple device and efficient methods for the high throughput isolation of proteins sequestered in the periplasmic space fraction of procaryotic host cells. The high throughput device and methods described herein allows for the preparation of greater than 2500 periplasmic space fractions in a single day. The device and methods utilize filtration in combination with either positive or negative pressure to isolate periplasmic fractions. The use of filtration offers advantages over current methods within the art because it eliminates the time consuming need for centrifugation steps and allows for the simultaneous processing of multiple samples. These advantages are of great benefit to high throughput screening of recombinant proteins for drug development processes.

In one embodiment, the invention is directed to a device for simultaneously isolating periplasmic space fractions from multiple samples of host cells. The device is advantageous in that both the harvesting of bacteria and the isolation of periplasmic space fractions can be performed using the same apparatus. The device consists of a vacuum chamber which is open at one end to support a 96 well sample chamber. The 96 well sample chamber is a multi-well plate wherein the bottom of each well consists of a membrane filter in which periplasmic space fractions can pass through. The 96 well sample chamber contains filter membranes attached to the bottom of each of the individual wells. The device additionally contains supports inside the vacuum chamber to hold a 96 well collection chamber. A vacuum aperture is located within one wall of the device for attachment to a vacuum source 12. Multiple high throughput devices can be, for example, connected in series to simultaneously process multiple 96 well sample chambers.

In another embodiment, the invention is directed to a method for simultaneously isolating periplasmic fractions from multiple samples of host cells. The method utilizes the high throughput device above and consists of a two-step process for the rapid and efficient isolation of periplasmic space fractions. A 96 well or other multi-well format is employed to isolate fractions and screen multiple different samples in large scale for a periplasmic protein exhibiting a desired property. In the first step, samples of host cells harboring periplasmic proteins of interest are transferred from culture tubes to a 96 well sample chamber 11. A different host cell sample is placed in each of the different wells. The sample chamber contains a porous material such as a semi-permeable membrane at the bottom of each well. The porous material allows passage of small molecules such as proteins and other macromolecules but is impermeable to larger particles such as membranes, organelles and whole cells, including bacteria. Negative pressure is applied to the vacuum chamber to remove culture media and sediment the host cells onto the porous material at the bottom of the wells. A collection chamber 10 is then placed inside the vacuum chamber and the sample chamber containing the host cells is replaced on top of the device. The outer membrane of the host cells is removed by digestion with lysozyme and negative pressure is again applied to remove contents released from the periplasmic space following lysozyme digestion. Periplasmic space fractions in the collection chamber are then screened by ELISA, for example, to identify the protein or proteins that exhibit the desired characteristic.

In yet another embodiment, the invention is directed to a workstation. The workstation consists of the device described above for harvesting and isolating periplasmic space fractions as well as another device for simultaneously growing a plurality of samples in a multi-well sample chamber format. The device for cultivating a plurality of bacterial samples is a rack which can be securely attached to a shaker incubator or the like. The rack holds up to 30 multi-well culture chambers with a capacity of about 2 ml of culture media for bacterial growth. Using a 96-well format culture chamber, the rack is therefore capable of simultaneously cultivating 2880 different bacterial samples. Additionally, the rack can be stacked on top of each other to increase the cultivation capacity of the incubator. In this configuration, a standard shaking incubator can be used to simultaneously cultivate about 8640 different bacterial samples if three racks are stacked on top of each other. The methods for simultaneously isolating periplasmic space fractions are used in conjunction with the devices of the workstation to achieve rapid and high throughput screening of samples.

The expression of genetically engineered proteins into the periplasmic space of procaryotic organisms allows for an enriched source of starting material for large scale isolation or screening of recombinant proteins. The periplasmic space is the region between the inner membrane and outer wall of procaryotic organisms such as gram negative bacteria. Expression of recombinant proteins into this space compartmentalizes and segregates the recombinant protein from the large majority of cytoplasmic proteins within the organism. Although there are endogenous proteins expressed within the periplasmic space, the relative number of periplasmic proteins is substantially smaller compared to cytoplasmic proteins. Thus, directed expression to the periplasmic space offers an initial and significant enrichment step by isolating only the periplasmic proteins away from cells and their contents.

The invention provides a high throughput device for simultaneously isolating periplasmic fractions from multiple samples of host cells. The high throughput device consists of a vacuum chamber having one end open, a means for supporting a collection chamber and a vacuum aperture. The open end of the vacuum chamber contains a means for supporting a sample chamber which can be sealed under vacuum.

In its simplest form, the high throughput device of the present invention (as shown in FIG. 1) contains a vacuum chamber 1 or positive pressure chamber which supports both a sample chamber and a collection chamber (shown in FIG. 3). The vacuum chamber, for a example can be of any size or shape depending on the desired use and on the availability of complementary sample and collection chambers. For example, the vacuum chamber can be round, square or rectangular so long as complementary sample and collection chambers are available or can be made available. For practical purposes, the shape of the vacuum chamber is such that it supports commercially available sample and collection chambers such as test tubes, petri dishes, tissue culture dishes of various sizes and formats and multi-well plates such as ELISA plates.

The size and format of the sample chamber and collection chamber will depend on the particular application. For example, if it is desired to perform a single large scale isolation of a periplasmic protein, then the vacuum chamber should be fitted with collection and sample chambers that have a single well format. Alternatively, if multiple samples are to be processed then the high throughput device should be fitted with chambers with multi-well formats. Particularly advantageous is the use of multi-well formats such as 96 well sample chambers that are standard for ELISA type assays and the like. In such a case, the vacuum chamber will be rectangular in shape to support the ELISA type sample and collection chambers and would be substantially similar to the vacuum chamber shown in FIG. 1.

The vacuum chamber is generally constructed of plastic or similar material that can be produced from a mold or that is easy to fasten together and withstand the moderate pressure forces that are necessary for the isolation of periplasmic space fractions. The joints of the chamber should also be sealed to prevent air leaks under negative or positive pressure which if occur, would cause a reduction in efficiency of the device. Materials other than plastic can alternatively be used to construct the vacuum chamber, however, some alternative materials may require the joints to be sealed by means of a gasket or the like to ensure efficiency of the device. Those skilled in the art will know how to construct the chamber to achieve the appropriate seals.

Figure 3A:
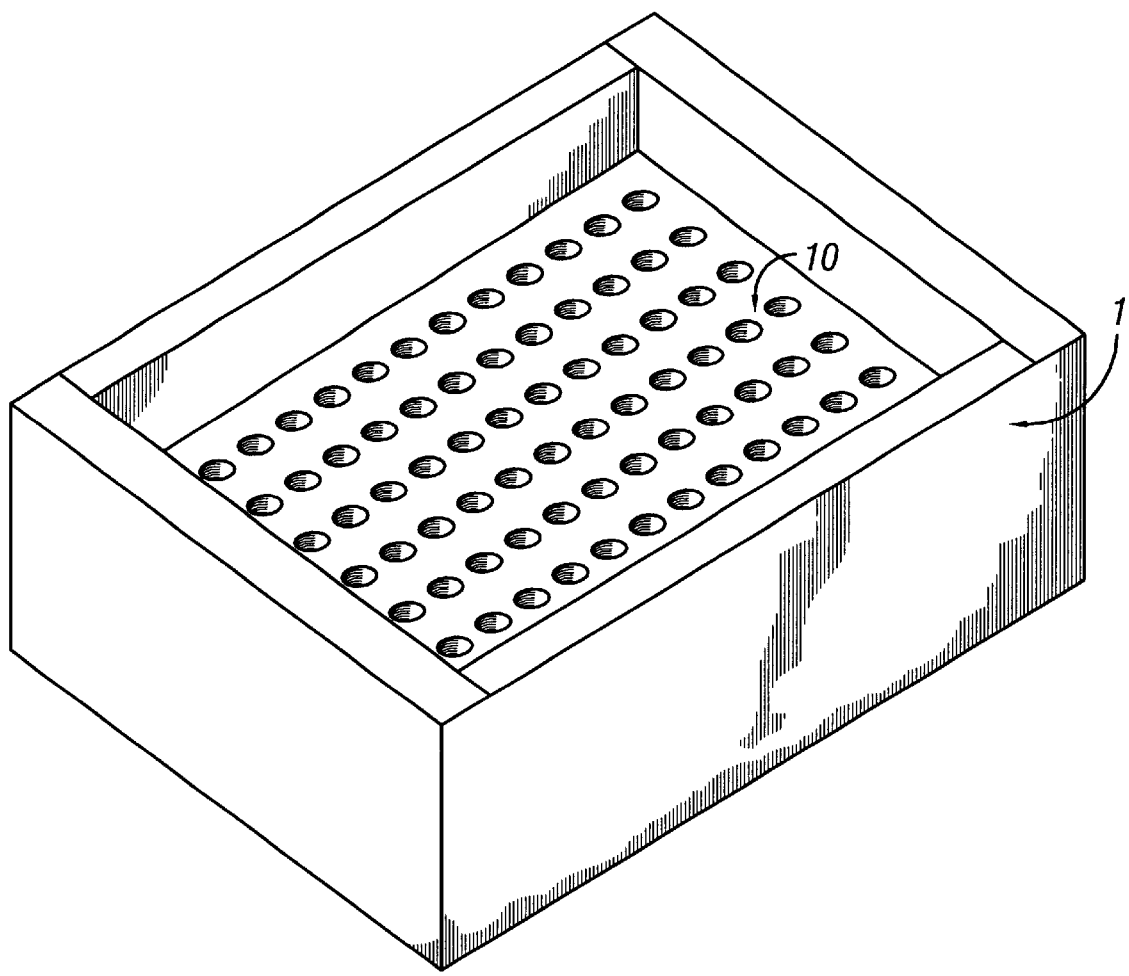
FIG. 3a is a schematic of a high throughput device for simultaneously isolating periplasmic fractions which exemplifies the placement of a 96 well collection chamber.
Figure 3B:
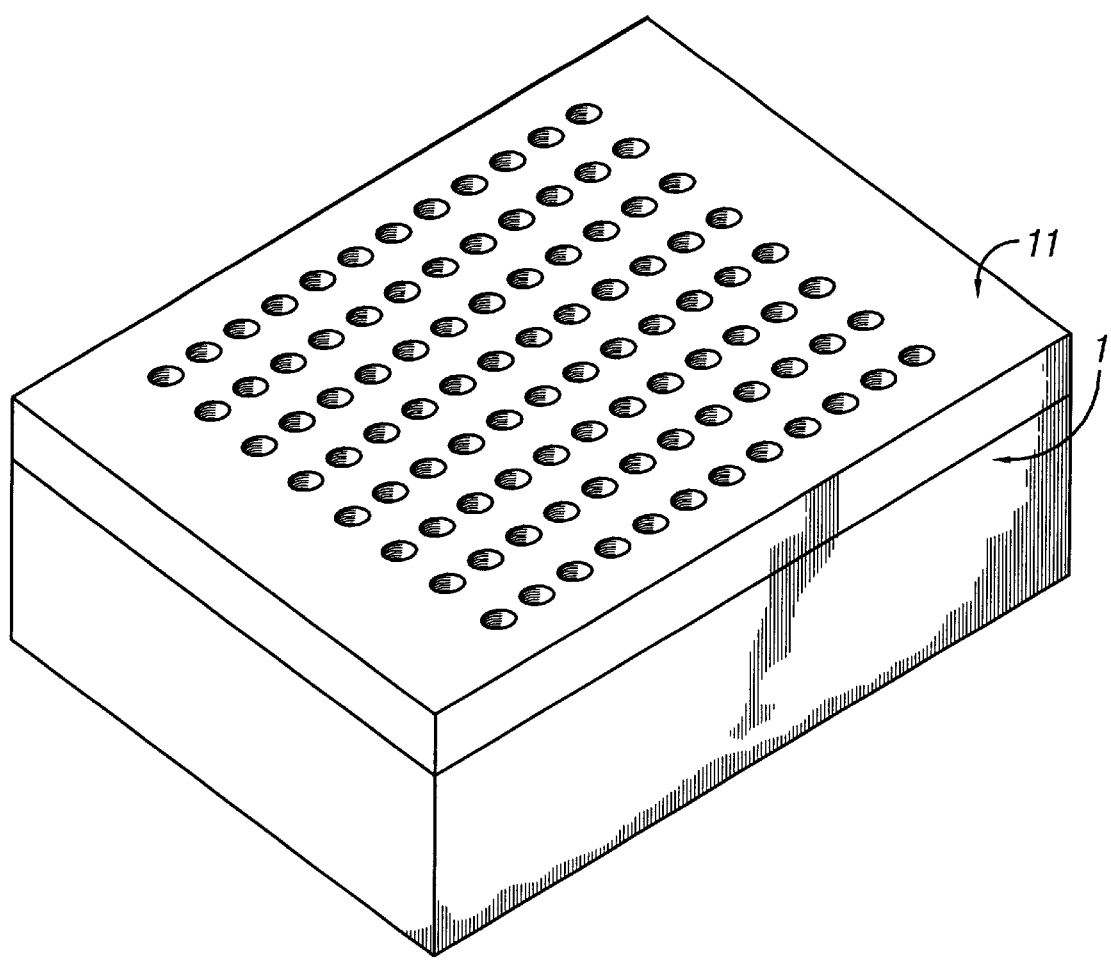
FIG. 3b is a schematic of a high throughput device for simultaneously isolating periplasmic fractions which exemplifies the placement of a 96 well sample chamber.
Figure 4:
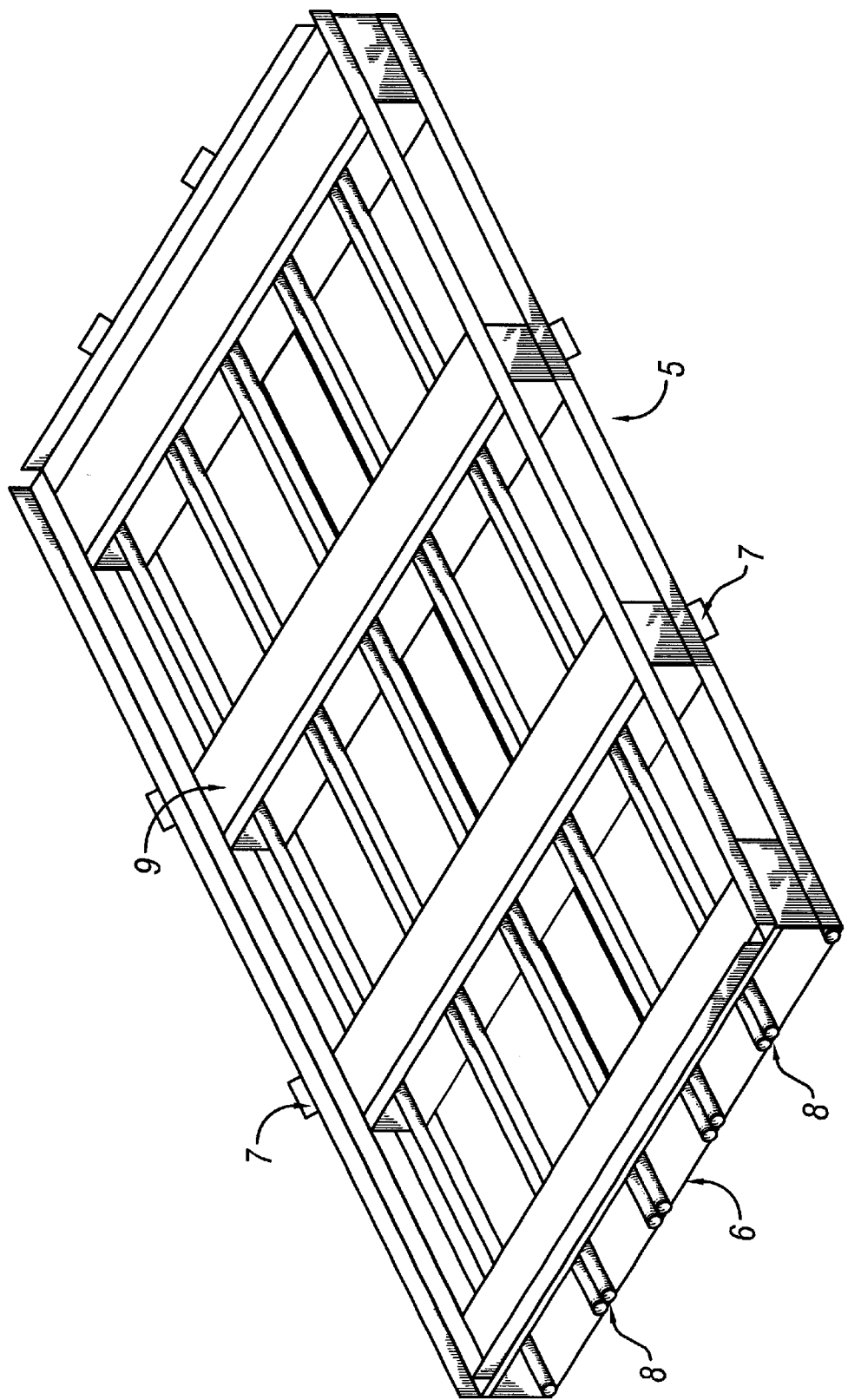
FIG. 4 is a schematic of a device for holding multi-well culture chambers for the simultaneous cultivation of bacterial samples.

The vacuum chamber of the high throughput device has one end open to allow vacuum pressure to be transferred from the vacuum chamber to the sample chamber. The vacuum chamber also contains a means for supporting a sample chamber 4 such as a ledge or shelf (FIG. 1). Shown in FIG. 3b is the vacuum chamber supporting a 96 well ELISA plate as the sample chamber. The means for supporting the sample chamber in FIG. 4 is the top ledge of the vacuum chamber. As with the seals of the vacuum chamber, the sample chamber is similarly supported so that there is an air-tight seal between it and the vacuum source. Similarly, the sides of the sample chamber should be sealed if necessary to prevent air flow around the chamber which will decrease efficiency. Gaskets, for example, are useful to accomplish these seals, however, other means known in the art can alternatively be used. In the alternate case of isolating samples by positive pressure, the seal should be between the source of pressure and the sample chamber.

Placement of the sample chamber can be, for example, on top of the vacuum chamber as shown in FIGS. 1 and 3b or, alternatively, a supporting means for the sample chamber can be placed just inside of the open end. As described above for efficient operation of the device, the supporting means should be capable of being sealed with the sample chamber under negative or positive pressure. Various materials which allow for the sealing of two chambers under vacuum are known by one skilled in art and include, for example, rubber, silicone and grease.

In addition to a means for supporting a sample chamber, the vacuum chamber also requires a means to support a collection chamber 2 (FIG. 1). The means to support the collection chamber can be, for example, substantially planer protrusions from one or more sides of the vacuum chamber or, alternatively, pedestals extending up from the bottom of the vacuum chamber can be used. Shown in FIG. 1 are two supports located on parallel sides of the vacuum chamber. FIG. 3a shows the vacuum chamber with a 96 well collection chamber placed on the two supports. The collection chamber can also be designed such that it contains a means for supporting itself within the vacuum chamber. Thus, the means supporting the collection chamber does not necessarily have to be a permanent part of the vacuum chamber.

For proper collection of periplasmic space fractions, the collection chamber is of similar format as the sample chamber to avoid inappropriate mixing of the fractions as they are drawn through the porous material of the sample chamber. The collection chamber is ideally placed, for example, directly under the sample chamber within the vacuum chamber. The sample and collection chambers can additionally be held in register by, for example, pins or complimentary groves, notches or the like to ensure accurate placement of the collection chamber under the sample chamber. Also, to ensuredrawing of the fractions directly below and into the collection chamber, the collection chamber is placed above the vacuum aperture when, for example, when negative pressure is employed. However, other placements of the collection chamber relative to the vacuum aperture can be used without substantially affecting the efficiency of the device. Such other placements are known by one skilled in the art. Similarly, the same cautions regarding pressure flow relative to sample location should be employed when using positive pressure. For example, it is efficient to have the pressure aperture located directly above the sample chamber. In this configuration a dome or canopy having an air-tight seal is placed directly over the vacuum and sample chambers (described further below).

A vacuum aperture 3 which can be fitted, or made to be fitted with a vacuum source is also present on the vacuum chamber (FIG. 1). The vacuum aperture can be any size or shape depending on the desired application but is typically round and fitted with a cylindrical nozzle. A vacuum hose can be attached to the cylindrical nozzle. The vacuum pressure can be controlled by a valve or a variety of other means known to those skilled in the art.

The high throughput device for simultaneously isolating multiple periplasmic fractions has been described above for use with negative pressure such as vacuum. However, the high throughput device can also be used with positive pressure. All that is necessary for isolating periplasmic fractions with positive pressure is to relocate the vacuum aperture above the sample chamber and apply pressure instead of vacuum. Relocation of the vacuum aperture above the sample chamber can be accomplished by, for example, the use of a manifold which fits over the sample chamber or by placing a compartment above the sample chamber which contains an aperture for connection to a pressure source. One skilled in the art will know how to modify and use the device with positive pressure giving the teachings described herein.

The invention also provides a high throughput device for simultaneously isolating periplasmic fractions from multiple samples of host cells. The high throughput device consists of a plurality of vacuum chambers connected to a vacuum source. Each of the vacuum chambers have one end open, a means for supporting a collection chamber and a vacuum aperture. The open end contains a means for supporting a sample chamber which can be sealed under vacuum.

Figure 2:
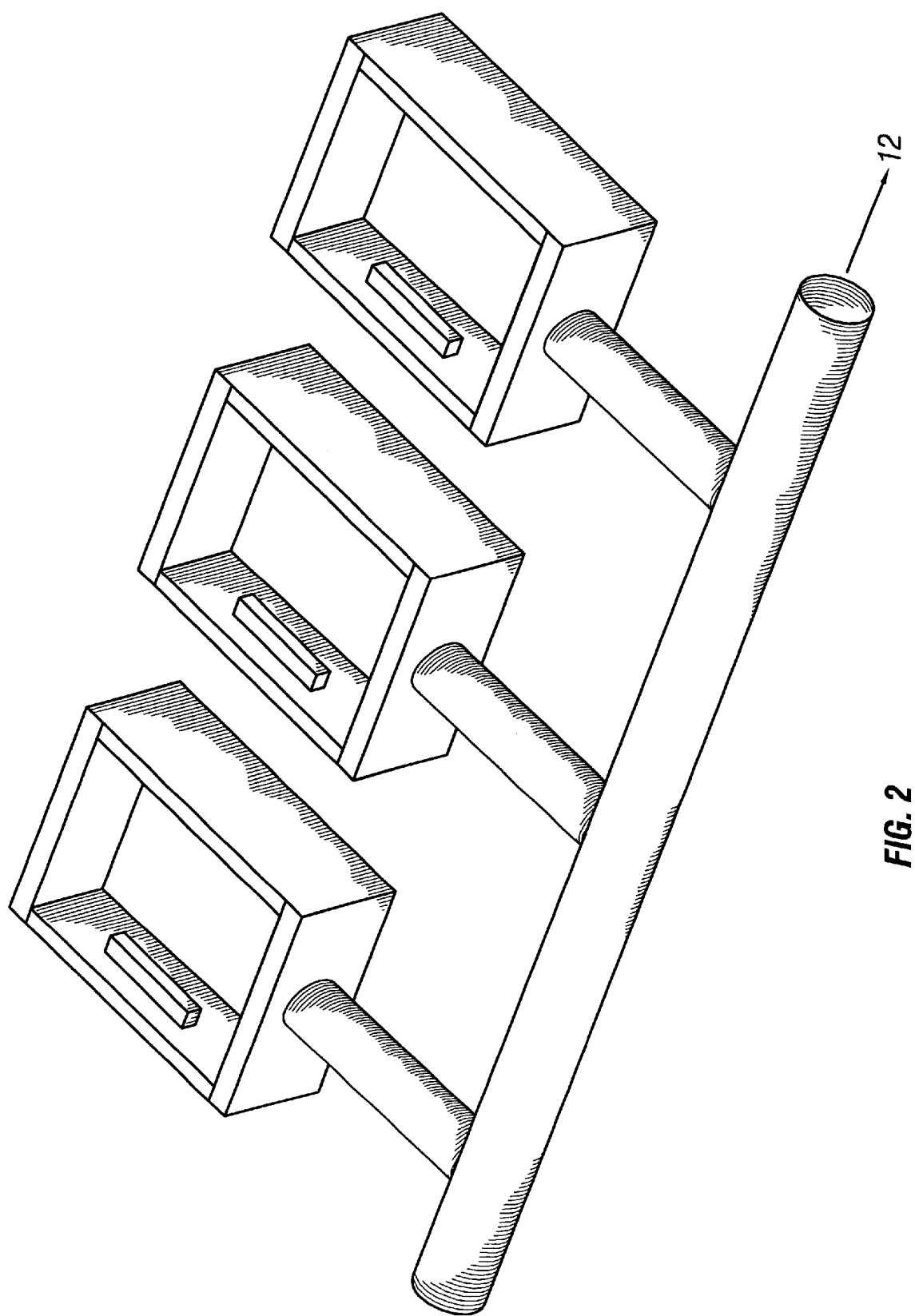
FIG. 2 is a schematic of a high throughput device for simultaneously isolating periplasmic fractions which exemplifies a plurality of vacuum chambers connected to a vacuum source in series.

The high throughput device previously described can be, for example, connected together to one or more duplicate devices and used for the simultaneous isolation of a plurality of multiple format sample chambers. In such a case, each sample chamber is supported by a vacuum chamber and the plurality of vacuum chambers are connected to a vacuum source. A schematic of such a plurality of vacuum chambers connected together is shown in FIG. 2. The vacuum chambers can be, for example, connected in series (FIG. 2) or in parallel. Using a 96 well format sample chamber, one skilled in the art can routinely isolate periplasmic fractions from about 1,000 different samples using only 10 or 11 vacuum chambers. Thus, the high throughput device allows for the simultaneous isolation of periplasmic fractions from many more than what can be accomplished with just a single vacuum chamber.

The invention also provides a device for the simultaneous cultivation of a plurality of samples. The device consists of a bottom component for supporting multi-well culture chambers, a top component for securing the culture chambers and a means for attaching the device to a shaker incubator.

The device for simultaneously cultivating a plurality of samples or, culture device, is described herein for the cultivation of, for example, bacterial samples. However, the device can be used for the simultaneous cultivation of essentially any species or organism which can be grown in liquid media in culture tubes or flasks. One advantage of the device is that it allows adequate aeration of samples grown in "culture tube" format. Aeration can be achieved in such multi-well format because the chambers can be securely fastened to allow shaking or orbital rotation and therefore adequate mixing of air similar to that achieved with a culture flask. The device is shown in FIG. 4.

In one form, the device for simultaneously cultivating a plurality of samples 5 can be described as a rack with a bottom component 6 for securely supporting multi-well culture chambers. The lower component functions to support multi-well chambers by acting as a platform. This platform can be shaped in a variety of sizes so long as it fits, or can be made to fit into a shaker or orbital incubator, or other functionally similar incubator. Thus, the bottom component of the rack can be, for example, a solid platform or the frame of a platform such as that shown in FIG. 4.

The bottom component also contains a means for supporting multi-well culture chambers 8. Such means can be, for example, a series of parallel guides or channels which fit over a complementary lip or protrusion on the culture chamber. Alternatively, means other than parallel guides, such as individual fasteners and the like can be used to attach the sample chambers to the device. Such alternative means are known to those skilled in the art. An example of a bottom component with parallel guides is shown in FIG. 4. For the purpose of illustration, a multi-well culture chamber having a dimension of, for example, 11 cm×7.4 cm can be mounted on a base of slightly larger size (12.9 cm×8.6 cm). The base then acts as the protrusion in which the guides or channels fit over to secure the culture chamber in place. For this specific example, the lower component of the rack can be configured for a standard laboratory shaker to hold about 30 of the above size culture chambers in a 5×6 array. A full complement of 6 culture chambers per row is required to secure the culture chambers uncontrolled horizontal motion. The parallel guides secure the culture chambers from uncontrolled vertical motion. The bottom component must also be secured at each of its ends to prevent the culture chambers from lateral, end-to-end motion. Securing the ends can be accomplished once the top component is in place by, for example, a removable gate or straps which can also function as a means for attaching the rack to a shaker incubator (see below).

The device for simultaneously cultivating a plurality of samples 5 also contains a top component 9 which aids in securing the culture chambers in place. As with the lower component, the top component is similarly a large planar surface which can be, for example, a solid platform structure or an open frame such as that shown in FIG. 4. The top component is attached by, for example, vertical supports which also serve to stabilize the rack when fully loaded with samples. The supports can be of any size or shape so long as they impart sufficient stability onto the rack as assembled and of sufficient strength to hold further loads placed on top. Such additional loads can be, for example, one or more racks placed on top to increase the capacity of the culture device for simultaneous cultivating a plurality of samples. Thus, when completely assembled, the culture device functions as a cage to stably enclose the sample chambers when they are being rotated or shaken within a shaker incubator.

When formatted to allow the secure placement of an additional rack on top, this stacking configuration can hold up to about 3 individual racks stacked on top of one another. Essentially, the number of racks which can be stacked on top of one another will be limited only by the size of the shaker incubator and the strength of the material used in the construction of the rack. Thus, for larger capacities, stronger materials should be used to support a larger number of racks in a stacked configuration.

The device for simultaneous cultivating a plurality of samples also contains a means for attaching to an incubator or shaker platform or the like. The means can be any of a variety of fasteners, buckles, clamps or belts known within the art so long as such attachment means are of sufficient strength to hold the cultivating device in place when fully loaded under shaker speeds normally used by those skilled in the art. For example, the attachment means can be fasteners such as screws or bolts which directly secure the bottom component to the incubator platform. Alternatively, and one particularly advantageous attachment means is the use of belts or straps because they can be used without significant alterations when the culturing device is used in a stacking configuration. Rubber mats placed between the lower component and the incubator platform can additionally be used because they increase the friction, and therefore reduce the tendency of the culturing device to slide during orbital motion within the incubator. Similarly, such rubber mats can be placed between the racks when used in a stacking configuration.

Briefly, for the use of straps as an attachment means, the shaking platform is, for example, modified to house several buckles attached directly to the platform. Such buckles can be attached using fasteners known within the art such as bolts or screws. A rubber mat is placed on top of the stacking platform, followed by the culturing device. The culturing device is secured by straps which pass over the rack and through the buckles.

When used in the stacking configuration the top component of the culturing device can contain a lip, for example, which further aids in the placement of another rack on top of the first. Such a lip can further have round slots or other functionally similar modifications to receive pins or the like which have been placed along the bottom component of the second rack. Thus, when placed in register, the pins and slots function to further stabilize the stacking of individual racks. The straps for attachment can then go around both racks of the culturing device to hold them firmly in place. Similarly, when stacking three or more, the same format or configuration can be used.

In the specific example described above where there are three culture devices in a stacked configuration and each culture device holds a 96 well culture chamber in a 5×6 array, the culture capacity of each rack is 30×96 or 2880 different samples. Tripling this number for the stacked configuration allows for the simultaneous culturing of at least 8640 different samples. Thus, when used in conduction with the high throughput device for simultaneous processing of a plurality of periplasmic space fractions, these two devices yield an efficient and cost effective workstation for discovery of new biological compounds and pharmaceuticals.

The invention provides a method for simultaneously isolating periplasmic fractions from multiple samples of host cells. The method consists of: (a) providing a high throughput device for simultaneously isolating periplasmic fractions from multiple samples of host cells having a vacuum chamber containing one end open, a means for supporting a collection chamber and a vacuum aperture, the open end of the vacuum chamber having a means for supporting a sample chamber which can be sealed under vacuum; (b) attaching the sample chamber containing a sample of host cells in media to the vacuum chamber; (c) applying a vacuum to the vacuum chamber to remove the media; (d) removing the outer membrane of the host cells; (e) attaching a collection chamber to the vacuum chamber; and (f) applying a vacuum to the vacuum chamber to collect the periplasmic fraction from the host cells.

Proteins expressed within the periplasmic space of host cells can be rapidly and efficiently prepared by the methods described herein. Such proteins can be, for example, recombinant proteins or those that are naturally occurring and endogenous to the host cell. A "host cell" as used herein, is any cell such as those of procaryotic origin which have a periplasmic space or similar compartment which is separated by an inner membrane and outer cell wall. The method is particularly advantageous when used to screen a large population of recombinant proteins such as a library and identify one or more proteins within the library which exhibit a desired characteristic. Such a use is described below in Example I.

As with the high throughput device described previously, the method can be use in essentially any desired format to simultaneously isolate periplasmic fractions from one to thousands of different samples. The method will be described with reference to the simultaneous isolation of 96 different periplasmic fractions using a standard ELISA type plate as a sample chamber. One advantage of using a 96 well format for both culturing and sample preparation procedures is that there are many devices available for simultaneously dispensing and manipulating multiple samples within such a format. Moreover, several automated procedures have been devised which manipulate and process samples in a 96 well format. The methods described herein can similarly be automated to further increase the speed and efficiency of the high throughput isolation of periplasmic fractions. One skilled in the art will know how to employ the methods described herein to isolate either smaller or larger numbers of fractions depending on the desired need.

The high throughput device described previously is used in the methods for simultaneously isolating periplasmic fractions from multiple samples of host cells. The vacuum chamber of the device can be used alone to simultaneously isolate up to 96 different periplasmic fractions. Alternatively, one or more additional vacuum chambers can be used in combination to isolate greater than 96 different periplasmic fractions.

Host cells expressing the periplasmic protein or proteins are grown to optimal density in culture media. The media and density will depend on the host strain and the desired level of expression. Such medias and procedures for expression are known by one skilled in the art and are described in standard laboratory manuals such as Sambrook et al., *Molecular Cloning: A Laboratory Manual*, Cold Spring Harbor Laboratory, New York (1992) and Ansubel et al., *Current Protocols in Molecular Biology*, John Whiley and Sons, Baltimore, M.d. (1989). Specific procedures for periplasmic expression are also well known in the art and are described, for example, in Skerra and Pluckthun, *Science* 240:1038 (1988) and Oka et al., *Proc. Natl. Acad. Sci. USA* 82:7212 (1985).

For the simultaneous isolation of periplasmic fractions from 96 different samples a culture chamber is used which is constructed to contain 96 culture tubes in an 8×12 array. Each of the culture tubes within the chamber can hold between about 0.1 mls to greater than about 5 mls of media. Culture chambers holding smaller or larger volumes can similarly be used. The culture chambers are inoculated with the host cells and secured in a shaker incubator by braces which attach to the shaker apparatus. Alternatively, host cells can be grown using various types of culture tubes or flasks known by those skilled in the art.

Following the appropriate period of growth, most cells are transferred from the culture chamber to a ample chamber. Transfer of samples can be accomplished by, for example, using a dispenser which is appropriately formatted into a multi-well configuration. The sample chamber contains, for example, a porous material such as a semi-permeable membrane at the bottom of each sample well (in the case of a 96 well sample chamber). The porous material should be selected such that it is permeable to small molecules and macromolecules such as proteins but not to large particles and cells. There are many such materials known to one skilled in the art and include, for example, filter membranes such as those which exclude specific size particles and membranes which exclude specific molecular weights of macromolecules. Such membranes can include both naturally occurring membranes and synthetic membranes such as nylon and the like. A specific example of a 96 well sample chamber which contains such a porous material is the SM120L P plate supplied by Pall Corporation (Portsmouth, England). This sample chamber contains a neutral nylon membrane with an average pore diameter of about 1 micron.

Once transferred to the sample chamber, media is removed by using, for example, vacuum to draw the media through the porous material and host cells are sedimented to the bottom of each well. If it is desirable to isolate more protein than what is available from a single well, then more host cells from the culture can be dispensed into the appropriate wells and the procedure repeated.

To isolate periplasmic space fractions, the outer wall of the sedimented host cells is removed without compromising the integrity of the inner membrane. Removal of the outer wall in this fashion releases the contents between the outer wall and inner membrane into the well. Removal of the outer wall can be accomplished using a variety of different methods known to one skilled in the art. Such methods include, for example, digestion with lysozyme, sonication, osmotic lysis or chemical removal. Lysozyme treatment is most advantageous because it is efficient, very reproducible and can be performed simultaneously on multiple samples within a very short time period.

Once the periplasmic contents are released into the sample chamber, a collection chamber is placed onto the supports within the vacuum chamber and the sample chamber is placed above it on top of the vacuum chamber. Vacuum is again applied and the periplasmic contents are drawn through the porous material into the collection chamber. With the inner cell wall remaining intact, host cells and their cytoplasmic contents are left behind in the sample chamber. Proteins within the periplasmic space fractions can then be analyzed for the desired activity or purified for other desired uses.

Thus, the invention also provides a workstation. The workstation consists of a device for simultaneously cultivating a plurality of samples and a device for simultaneously isolating a plurality of periplasmic space fractions. The device for simultaneously isolating a plurality of periplasmic space fractions can be a vacuum chamber which is useful for both the harvesting of samples and the subsequent isolation of periplasmic space fractions. The devices of the workstation employ the methods described herein to achieve the high throughput isolation of a multitude of periplasmic space fractions.

It is understood that modifications which do not substantially affect the activity of the various embodiments of this invention are also included within the definition of the invention provided herein. Accordingly, the following examples are intended to illustrate but not limit the present invention.

Example I Simultaneous Isolation of Periplasmic Space Fractions From Multiple Samples of Host Cells This Example shows the functional analysis of proteins present in periplasmic samples prepared by the high throughout device and compares their activity to those isolated by manual procedures. Specifically, the functional activity of a randomly selected BR96 Fab variant prepared by both methods was assessed by measuring binding to tumor antigen.

BR96 is a chimeric antibody that recognizes a tumor-associated antigen belonging to the $Le^Y$ class of carbohydrate antigens. The BR96 antigen is expressed at high levels on the majority of carcinomas of the breast, lung, colon, and ovary.

BR96 heavy and light chain variable region genes were cloned into a M13 bacteriophage antibody Fab fragment expression vector which directs the periplasmic expession of assembled Fab fragments (Huse et al., *J. Immunol.* 149:3914 (1992)). From these initial clones, a library consisting of mutations introduced into complementarity determining region (CDR) 3 of the BR96antibody heavy chain gene was screened with synthetic $Le^Y$ probe and 12 individual clones found to be reactive with the probe. These clones were selected for the comparative analysis. Because these 12 clones contain mutations in heavy chain CDR 3, a region found to be involved in antigen binding, they exhibit a range of different binding activities to $Le^y$.

Each of the 12 selected variant BR96 bacteriophage clones was used to infect a 5 ml culture of bacterial strain MK30-3 and all 12 cultures were grown as described in Huse et al. (supra) or in Glaser et al. (*J. Immunol.* 149:3903 (1992)). At the appropriate density, 200 µl aliquots of each culture were harvested from each of the 12 cultures and used to prepare periplasm samples with the high throughout device and periplasm samples by manual procedures. Such manual procedures are known to those skilled in the art and can be found described in Huse et al. (supra), Skerra and Pluckthun, *Science* 240:1038 (1988) and in Oka et al. *Proc. Natl. Acad. Sci. USA* 82:7212 (1985).

Briefly, preparation of periplasm samples with the high throughput device proceeded as follows. The 200 µl aliquots were each placed in individual wells of the sample chamber of the high throughput device. The sample chamber selected was a Silent Monitor Loprodyne 1.2 µ membrane-bottomed plate (Pall Corporation, Portsmouth England). Vacuum was applied until the medium was removed and the bacteria had sedimented to the bottom of each well. A 100 µl/well of freshly prepared 30 mM Tris-HCl, 2 mM EDTA, 20% sucrose pH 8.0 containing 1 mg/ml lysozyme was then added followed by incubation at room temperature for 10 minutes.

To simultaneously collect each periplasmic space fraction a collection chamber was placed below the sample chamber. To ensure that both the collection and sample chambers were in register, a modification of the device was performed to contain pins that position the membrane-bottomed sample chamber in register with the collection chamber. Vacuum was again applied until periplasm samples were collected into the collection chamber. These samples were then stored until used in the functional comparison.

To prepare periplasmic space samples by manual methods methods, 200 µl aliquots from each of the 12 cultures described above were pipetted into 1.5 ml eppendorf tubes. The tubes were microcentrifuged at room temperature for 3 minutes at 8000 rpm. Pellets were resuspended in 100 µl 30 mM Tris-HCl, 2 MM EDTA, 20% sucrose pH 8.0 and 100 µl/well of freshly prepared 30 mM Tris-HCl, 2 mM EDTA, 20% sucrose pH 8.0 containing 1 mg/ml lysozyme was added. The mixture was incubated at room temperature for 10 minutes. Following incubation, the lysate was a microcentrifuged at 4° C. for 10 minutes at 9000 rpm. The supernatant containing periplasm fraction was collected and stored with the previously isolated samples.

A comparison of tumor antigen binding between periplasm samples prepared using the high throughput device and samples prepared by manual methods was performed by ELISA. Briefly, 96-well tissue culture plates seeded with H3396 cells were fixed and prepared for ELISA using methods known to those skilled in the art (Wolff et al., *Cancer Res.* 53:2560 (1993)). H3396 cells are known to express the $Le^Y$ antigen and are therefore reactive to BR96 antibody and Fab fragments in a cell based ELISA assay. Periplasmic samples from each of the 12 clones prepared by the manual method were first diluted 1:4 with Tris buffered saline containing 1% bovine serum albumin (TBSB). The same samples prepared with the high throughput device were left undiluted. 50 µl of periplasmic sample from each clone prepared by the manual method and the high throughput device was added per well to the H3396 plate and incubated at room temperature for 2 hours. The plate was washed four times with TBSB and 50 µl/well of a 1:1000 dilution of goat anti-human kappa chain alkaline phosphatase conjugate (Southern Biotech) was added and the plate incubated at room temperature for an additional 30 minutes. The plate was then washed four times with TBSB followed by two washes with TBS. The immobilized antibody conjugate was developed with 100 µl/well phenolphthalein monophosphate and absorbance measured at 560 nm.

Figure 5:
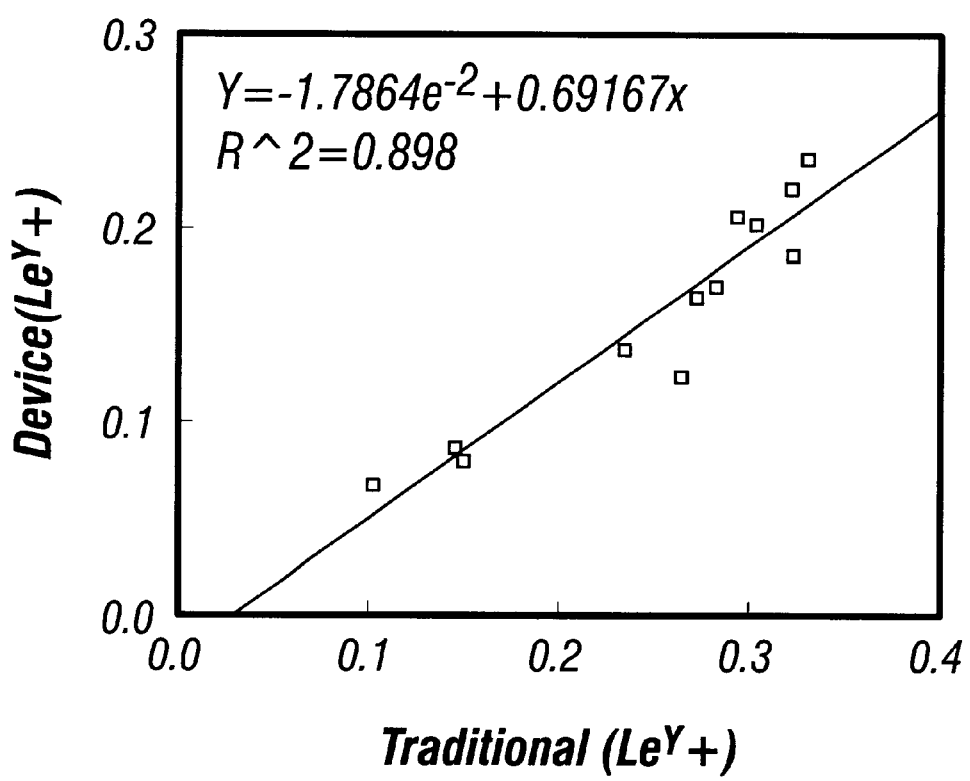
FIG. 5 shows a comparison of methods for preparing periplasmic space fractions.

The absorbance values obtained for each clone from the two methods of preparing periplasm were plotted and are shown in FIG. 5. The data demonstrates that samples prepared with the high throughput device bound tumor antigen similarly as those prepared by traditional methods. The high degree of correlation ($r^2=0.898$) indicates that samples prepared by the high throughput device accurately reflect protein binding properties over a range of activities as the same samples prepared by conventional methods. Secondly, the data demonstrates the device produces periplasm fractions containing functionally active protein.

Example II Screening of Periplasmic Space Fractions for High Affinity Varients

This example shows the simultaneous screening and identification of a high affinity variant of the BR96 antibody Fab fragment.

A library similar to that described in Example I was used for this procedure. However, instead of mutations within the CDR3 region, this library contained mutations introduced into CDR2 region of the BR96 antibody heavy chain gene. Screening of periplasmic fractions was performed following their preparation with the high throughput device.

Briefly, a library consisting of mutations introduced into complementarity determining region 2 of the BR96 antibody heavy chain gene was screened with a synthetic $Le^Y$ probe. A total of 88 individual clones were found to be reactive with the probe. These clones were selected for preparation of periplasm fractions with the high throughput device.

Figure 6:
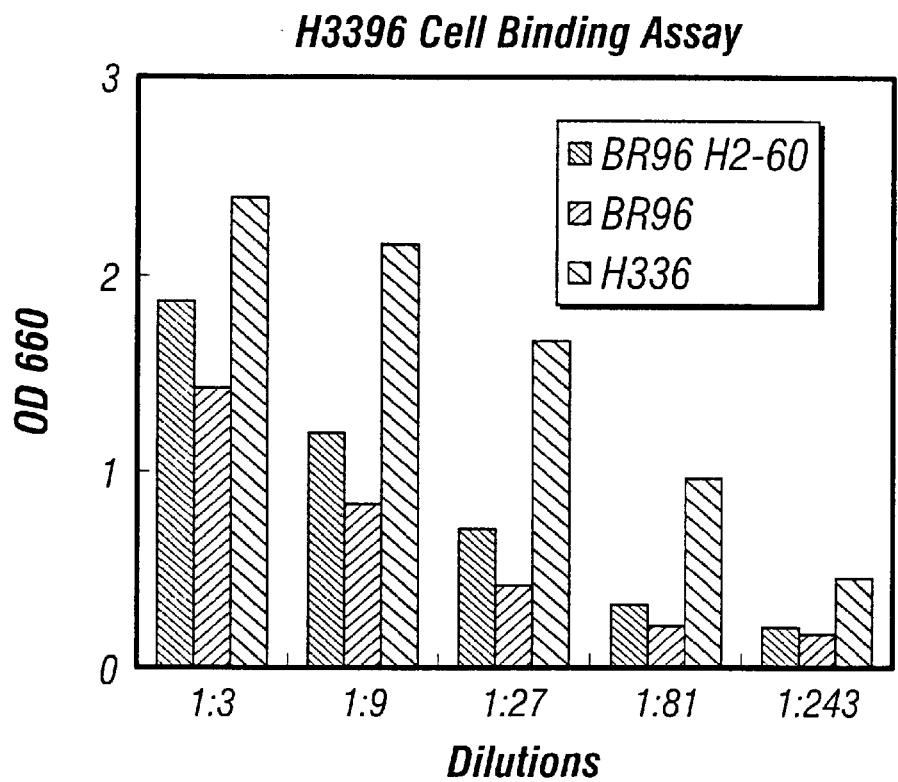
FIG. 6 is a comparison of antibody binding affinities prepared using the high throughput device.
Figure 6:
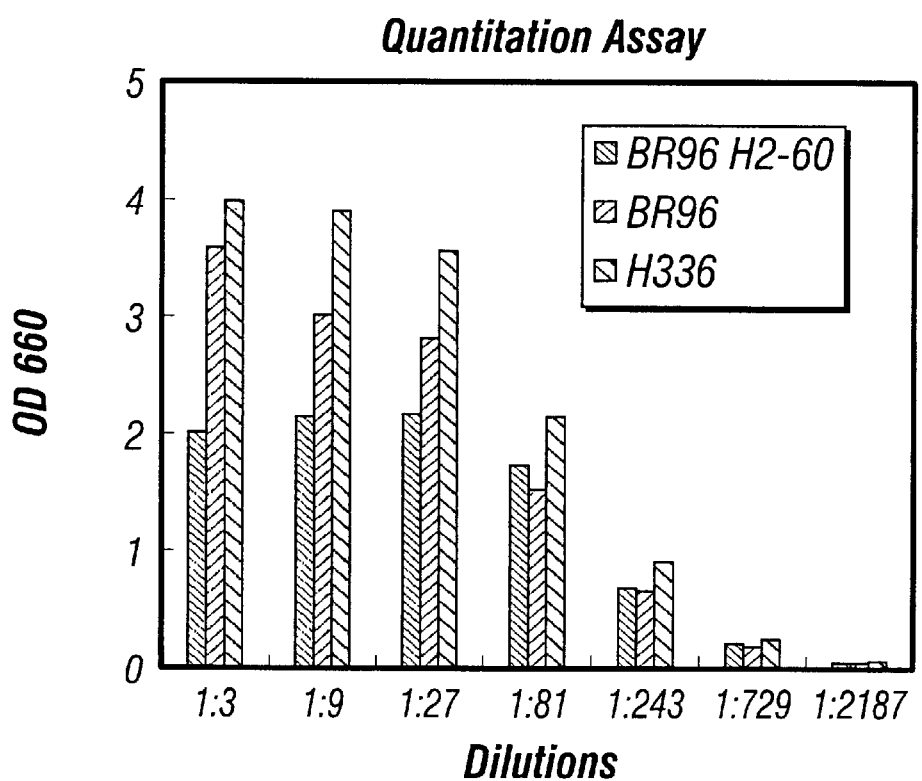

Each of the 88 selected variant bacteriophage clones was used to infect a 0.5 ml/well culture of bacterial strain MK30-3 in a 96 well culture chamber (DBM block; DBM Scientific). The culture chamber containing the samples were incubated in the device for simultaneously cultivating a plurality of samples. The infected cultures were incubated essentially as previously described in Example I. Following culturing, 200 µl aliquots were harvested from each of the wells and used to prepare periplasm samples with the high throughput device as previously described in Example I. These samples were then analyzed for binding to the H3396 tumor antigen by ELISA as previously described. The results are shown in FIG. 6.

FIG. 6A shows a clone, BR96 H2-60, that produces a Fab which binds tumor antigen greater than the parent BR96 molecule at all dilutions tested. BR96 H2-60was also found to synthesize less material than the parent BR96 clone (FIG. 6B). Given that binding to antigen by BR96 H2-60 is apparently stronger than BR96, and yet the total amount of BR96 H2-60 material by comparison is reduced, these data indicate that BR96 H2 th 60 has a higher intrinsic affinity for tumor antigen. These data also demonstrate that the high throughput device can prepare periplasm fractions of similar yet distinguishable properties which enables the identification of molecules with improved binding properties.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A device for isolating a periplasmic fraction of cells having an inner cell wall and an outer membrane, comprising:
    a vacuum chamber having an opening with means for supporting a sample chamber removably attachable to the opening and a vacuum aperture, and
    a removable sample chamber capable of containing the cells having an outer membrane, wherein the sample chamber is removably attached to the opening of the vacuum chamber, forming a vacuum-tight seal with the opening,
        wherein the sample chamber has a chamber wall that is a neutral nylon membrane having an average pore diameter of about 1 to about 1.2 micron, whereby the membrane of the chamber wall is permeable to periplasmic small molecules and macromolecules, but not permeable to cells having an intact inner cell wall.

2. The device of claim 1, wherein the sample chamber is in a multiple well format.

3. The device of claim 2, wherein the multiple well format is a 96-well format.

4. The device of claim 1, further comprising a removable collection chamber that is positioned within the vacuum chamber in relation to the sample chamber to collect the periplasmic small molecules and macromolecules that can pass through the membrane of the chamber wall.

5. The device of claim 4, wherein the collection chamber is in a multiple well format.

6. The device of claim 1, further comprising means for disrupting the outer membrane of cells in the sample chamber.

7. The device of claim 6, wherein the disrupting means is an enzyme.

8. The device of claim 7, wherein the enzyme is lysozyme.

9. The device of claim 1, wherein the device comprises a plurality of the vacuum chambers and the sample chambers.

10. The device of claim 9, wherein the vacuum apertures of the plurality of vacuum chambers are connected in series.

11. The device of claim 9, wherein the vacuum apertures of the plurality of vacuum chambers are connected in parallel.

12. The device of claim 1, wherein the periplasmic macromolecules are antibodies or antibody fragments.

13. A method for isolating a periplasmic fraction of cells, having an inner cell wall and an outer membrane comprising the steps of:
    (a) providing a vacuum chamber having an opening and a vacuum aperture;
    (b) attaching a sample chamber to the opening of the vacuum chamber, forming a vacuum-tight seal,
        wherein the sample chamber has a chamber wall that is a neutral nylon membrane having an average pore diameter of about 1 to about 1.2 micron, whereby the chamber wall is permeable to periplasmic small molecules and macromolecules, but not permeable to cells having an intact inner cell wall, (c) adding to the sample chamber, media that contains cells that have an inner cell wall and an outer membrane;

(d) applying a vacuum to the vacuum aperture to create a vacuum in the vacuum chamber, thereby removing the media from the sample chamber by the media passing through the membrane of the chamber wall;

(e) disrupting the outer membrane of the cells in the sample chamber; and (f) reapplying a vacuum to the vacuum aperture, thereby isolating a periplasmic fraction by the fraction passing through the membrane of the chamber wall, without cells having an intact inner cell wall passing through the membrane of the chamber wall.

14. The method of claim 13 wherein the sample chamber is in a multiple well format.

15. The method of claim 14, wherein the multiple well format is a 96-well format.

16. The method of claim 13, further comprising a step of providing a collection chamber in the vacuum chamber after step (d) positioned in relation to the sample chamber to collect the periplasmic small molecules and macromolecules that can pass through the membrane of the chamber wall.

17. The device of claim 16, wherein the collection chamber is in a multiple well format.

18. The method of claim 13, wherein the disrupting step uses enzymatic digestion.

19. The method of claim 18, wherein the enzymatic digestion uses lysozyme.

20. The method of claim 13, further providing a plurality of the vacuum chambers and the sample chambers.

21. The method of claim 20, wherein the vacuum apertures of the plurality of vacuum chambers are connected in series.

22. The method of claim 20, wherein the vacuum apertures of the plurality of vacuum chambers are connected in parallel.

23. The method of claim 13, wherein the periplasmic macromolecules are antibodies or antibody fragments.

* * * * *